United States Patent
Denuell et al.

(10) Patent No.: US 10,154,953 B2
(45) Date of Patent: Dec. 18, 2018

(54) USE OF A COMPOSITION FOR BLEACHING TEETH

(71) Applicant: BASF SE, Ludwigshafen am Rhein (DE)

(72) Inventors: Wolfgang Denuell, Mannheim (DE); Adrian Natalello, Hofheim (DE); Christian Schade, Ludwigshafen (DE); Dirk Mampe, Duesseldorf (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/566,745

(22) PCT Filed: Apr. 18, 2016

(86) PCT No.: PCT/EP2016/058510
§ 371 (c)(1),
(2) Date: Oct. 16, 2017

(87) PCT Pub. No.: WO2016/173871
PCT Pub. Date: Nov. 3, 2016

(65) Prior Publication Data
US 2018/0125773 A1 May 10, 2018

(30) Foreign Application Priority Data

Apr. 28, 2015 (EP) .................................... 15165457
Apr. 28, 2015 (EP) .................................... 15165458

(51) Int. Cl.
| | | |
|---|---|---|
| *A61K 8/81* | (2006.01) |
| *A61K 8/38* | (2006.01) |
| *A61K 8/22* | (2006.01) |
| *A61Q 11/00* | (2006.01) |
| *C08F 226/10* | (2006.01) |
| *C08F 230/02* | (2006.01) |
| *C08F 226/06* | (2006.01) |
| *C08F 222/02* | (2006.01) |
| *C08K 3/18* | (2006.01) |
| *C08K 5/14* | (2006.01) |
| *C08L 35/00* | (2006.01) |
| *C08L 39/04* | (2006.01) |
| *C08F 220/58* | (2006.01) |
| *C08K 3/20* | (2006.01) |

(52) U.S. Cl.
CPC .............. *A61K 8/8182* (2013.01); *A61K 8/22* (2013.01); *A61K 8/38* (2013.01); *A61K 8/817* (2013.01); *A61K 8/8176* (2013.01); *A61Q 11/00* (2013.01); *C08F 222/02* (2013.01); *C08F 226/06* (2013.01); *C08F 226/10* (2013.01); *C08F 230/02* (2013.01); *C08K 3/18* (2013.01); *C08K 5/14* (2013.01); *C08L 35/00* (2013.01); *C08L 39/04* (2013.01); *C08F 2220/585* (2013.01); *C08K 3/20* (2013.01)

(58) Field of Classification Search
CPC ........................................................ A61K 7/16
USPC ............................................................ 424/53
See application file for complete search history.

(56) References Cited

U.S. PATENT DOCUMENTS

| | | | |
|---|---|---|---|
| 5,260,391 A | 11/1993 | Stephens | |
| 5,753,770 A | 5/1998 | Breitenbach et al. | |
| 6,780,401 B2 * | 8/2004 | Kim ................... | A61K 8/0208 424/443 |
| 8,652,446 B2 * | 2/2014 | Kim ................... | A61C 19/066 424/49 |
| 8,815,215 B2 | 8/2014 | Prencipe et al. | |
| 2005/0036956 A1 | 2/2005 | Fei et al. | |
| 2008/0145321 A1 | 6/2008 | Zaidel et al. | |
| 2012/0058059 A1 | 3/2012 | Chopra et al. | |
| 2012/0301522 A1 | 11/2012 | Prosise et al. | |

FOREIGN PATENT DOCUMENTS

| | | |
|---|---|---|
| CA | 2152038 A1 | 12/1995 |
| DE | 4344131 A1 | 6/1995 |
| WO | WO-01/68045 A1 | 9/2001 |
| WO | WO-2011/130370 A1 | 10/2011 |

OTHER PUBLICATIONS

International Search Report for Patent Application No. PCT/EP2016/058510, dated May 24, 2016.

* cited by examiner

*Primary Examiner* — Walter E Webb
(74) *Attorney, Agent, or Firm* — Marshall, Gerstein & Borun LLP

(57) ABSTRACT

The present invention relates to the use of a composition comprising a peroxidic compound and a particular, generically defined copolymer for tooth bleaching.

14 Claims, No Drawings

USE OF A COMPOSITION FOR BLEACHING TEETH

CROSS-REFERENCE TO RELATED APPLICATIONS

This application is the U.S. National Stage application of International Patent Application No. PCT/EP2016/058510, filed Apr. 18, 2016, which claims the benefit of European Patent Application No. 15165458.9, filed Apr. 28, 2015 and European Patent Application No. 15165457.1, filed Apr. 28, 2015.

The present invention relates to the use of a particular, generically defined copolymer for stabilization of a peroxidic compound against breakdown. The present invention further relates to the use of a composition comprising a peroxidic compound and this particular copolymer for tooth bleaching. The present invention further relates to a particular embodiment of the copolymer, namely a copolymer comprising repeat units derived from N-vinylpyrrolidone and at least one comonomer which is selected from the group consisting of vinylphosphonic acid, 2-acrylamido-2-methylpropanesulfonic acid and combinations of these monomers.

It is known that hydrogen peroxide (also referred to hereinafter as $H_2O_2$ or H2O2) can be used as a bleaching agent in order to whiten the enamel and hence to bleach the teeth, also referred to as "teeth whitening". H2O2 is unstable in aqueous formulations at room temperature. Therefore, toothpastes comprising H2O2 are typically anhydrous in order to avoid or at least slow down premature breakdown of the H2O2 during storage. For example, toothpastes comprising a composition comprising urea and H2O2 that is also referred to as urea-H2O2 complex are known. There are also known toothpastes comprising a composition comprising polyvinylpyrrolidone (PVP) and H2O2. Such compositions comprising a polymer and H2O2 are often referred to as "complex of polymer and H2O2". In general, the stability of PVP-H2O2 complexes is higher than the stability of the urea-H2O2 complexes. What is meant in each case is the stability against breakdown of the H2O2.

Polymer-$H_2O_2$ complexes are also known from fields of use other than dental care and tooth bleaching.

WO 2011/130370 A1 describes copolymers having a molar mass Mw of 500 to 15 000 D, formed from a vinyl monomer having an amide group and a vinyl monomer having an acid group or the corresponding salt. Possible applications disclosed for the polymers are oilfield applications or corrosion protection. There is no description of the use of these copolymers for $H_2O_2$ complexes or for dental care.

DE 4344131 describes the preparation of polymer-$H_2O_2$ complexes by fluidized bed drying. Polymers mentioned explicitly are copolymers of N-vinylcaprolactam and (meth)acrylamidopropyl-3-sulfonic acid and copolymers of N-vinylpyrrolidone and methacrylic acid in a weight ratio of 20:1 to 1:20. It is stated that these polymers can be used as disinfectants or as preservatives for dental care. There is no clear disclosure of what can be disinfected or preserved, a dental care product or teeth.

WO 01/68045 describes anhydrous adhesive strips for tooth whitening, the adhesive layer of which consists of a peroxide, a peroxide stabilizer and a vitreous hydrophilic polymer. Polymers mentioned are polyvinylpyrrolidone and poly(vinylpyrrolidone-co-vinyl acetate).

US 2012/0058059 describes a monophasic toothpaste comprising $H_2O_2$-PVP complexes as bleaching agent. The PVP component has been crosslinked.

US 2005/0036956 describes a tooth bleaching composition comprising, as well as an $H_2O_2$-PVP complex, a compound having elevated tooth affinity. This compound can be a polymer. Examples mentioned are polycarboxylates or vinylpyrrolidone-vinyl acetate copolymers. No further copolymers are mentioned.

US 2012/0301522 describes an aqueous composition for dental treatment, comprising a complex of $H_2O_2$ and a vinyllactam polymer. Monomers mentioned for the polymers are N-vinylpyrrolidone and a multitude of other lactam monomers.

US 2008/0145321 describes a dental treatment composition comprising a complex of a peroxide such as $H_2O_2$ and a vinyllactam polymer. Monomers mentioned for the polymers are numerous lactam monomers, for example N-vinylpyrrolidone (NVP). Further polymers described are copolymers of NVP and vinyl acetate or dimethylaminoethyl methacrylate.

The action of known toothpastes for tooth bleaching that comprise a PVP-H2O2 complex is based on dissolution of the PVP-H2O2 complex on contact with saliva in the mouth and release of H2O2. This does not release the H2O2 specifically at the site of its desired effect, the surface of the tooth. It would therefore be desirable to release the H2O2 at the surface of the tooth, in order thus to provide it specifically at the desired site of action.

It is therefore an object of the present invention to stabilize a peroxidic compound, especially H2O2, against breakdown by means of those polymers that have a particular affinity for surfaces of teeth.

It would thus be possible to use corresponding compositions comprising such polymers and a peroxidic compound, especially H2O2, for tooth bleaching. At the same time, owing to the particular affinity of the polymers for tooth surfaces, the peroxidic compound, especially the H2O2, would be released to an enhanced degree at the surface of the tooth, and hence provided specifically at the desired site of action.

This object is achieved by the use of a copolymer defined hereinafter, which forms part of the subject matter of the present invention.

The present invention provides for the use of a copolymer comprising repeat units derived from at least one first monomer which is selected from the group consisting of N-vinylpyrrolidone (N-vinyl-2-pyrrolidone), N-vinyl-2-piperidone, N-vinyl-3-methylpyrrolidinone, N-vinyl-3-methylpiperidone, N-vinyl-3-methylcaprolactam, N-vinyl-4-methylpyrrolidinone, N-vinyl-4-methyl-2-pyrrolidone, N-vinyl-4-methylpiperidone, N-vinyl-4-methylcaprolactam, N-vinyl-5-methylpyrrolidinone, N-vinyl-5-ethyl-2-pyrrolidone, N-vinyl-4-methylpiperidone, N-vinyl-3-ethylpyrrolidinone, N-vinyl-4,5-dimethylpyrrolidinone, N-vinyl-5,5-dimethylpyrrolidinone, N-vinyl-3,3,5-trimethylpyrrolidinone, N-vinyl-5-methyl-5-ethylpyrrolidinone, N-vinyl-3,4,5-trimethyl-3-ethylpyrrolidinone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-2-caprolactam, N-vinyl-7-methylcaprolactam, N-vinyl-7-ethylcaprolactam, N-vinyl-3,5-dimethylcaprolactam, N-vinyl-4,6-dimethylcaprolactam, N-vinyl-3,5,7-trimethylcaprolactam, N-vinyl-2-valerolactam, N-vinylhexahydro-2-azepinone, N-vinyloctahydro-2-azocinone, N-vinyloctahydro-2-azoninone, N-vinyldecahydro-2-azecinone and combinations of these monomers, at least one comonomer which is selected from the group consisting of a monomer comprising at least one phosphoric ester group, a monomer comprising at least one phosphonic acid group, a monomer comprising at least one sulfonic acid group, an ethylenically unsaturated dicarboxylic acid, an ethylenically unsaturated dicarboxylic anhydride and combinations of these monomers, optionally at least one further free-radically polymerizable, ethylenically unsaturated monomer, especially at least one further free-radically polymerizable, ethylenically unsaturated monomer having an OH group or an OH group ethoxylated with 1 to 10 ethylene oxide units, especially 2-hydroxyethyl methacrylate (HEMA), and optionally at least one crosslinking comonomer having at least two free-radically polymerizable, ethylenically unsaturated groups in the molecule, for stabilization of a peroxidic compound against breakdown, wherein this peroxidic compound is selected from the group consisting of an organic peroxide compound and hydrogen peroxide, especially selected from the group consisting of an organic hydroperoxide and hydrogen peroxide, especially selected from the group consisting of tert-butyl hydroperoxide, cumene hydroperoxide and hydrogen peroxide, and is especially hydrogen peroxide.

In one embodiment of said use, the at least one first monomer is N-vinylpyrrolidone.

In one embodiment of said use, the at least one first monomer is N-vinyl-2-caprolactam.

In one embodiment of said use, the at least one comonomer is selected from the group consisting of maleic acid, maleic anhydride, fumaric acid, vinylphosphonic acid, 2-acrylamido-2-methylpropanesulfonic acid, acrylamidopropanesulfonic acid and combinations of these monomers.

In one embodiment of said use, the at least one comonomer is selected from the group consisting of vinylphosphonic acid, 2-acrylamido-2-methylpropanesulfonic acid and combinations of these monomers.

In one embodiment of said use, the at least one crosslinking comonomer is selected from the group consisting of N,N'-divinylethyleneurea, N,N'-divinylpropyleneurea, N,N'-divinylimidazolid-2-one, N-vinyl-2-ethylidenepyrrolidone, N-vinyl-3-ethylidenepyrrolidone, methylenebisacrylamide, an allyl ether, a vinyl ether, a (meth)acrylic ester, a (meth)acrylamide of an alcohol or of an amine having more than two functional groups, where the alcohol is preferably selected from the group consisting of ethylene glycol, diethylene glycol, butanediol, hexanediol, trimethylolpropane, pentaerythritol, polyethylene glycol, polypropylene glycol, and alkoxylated derivatives of said alcohols, and combinations of these monomers.

In one embodiment of said use, the copolymer, based on the total mass of the repeat units of the copolymer, 70%-99.5% by weight, preferably 80%-99% by weight, preferably 85%-98% by weight, of repeat units derived from the at least one first monomer, 0.5%-30% by weight, preferably 1%-20% by weight, preferably 2%-15% by weight, of repeat units derived from the at least one comonomer, 0% to 20% by weight, preferably 0% to 10% by weight, preferably 0% to 5% by weight, preferably 0% to 2% by weight, especially 0% by weight, of repeat units derived from the at least one further free-radically polymerizable, ethylenically unsaturated monomer, 0% to 10% by weight, preferably 0% to 2% by weight, preferably 0%-1% by weight, of repeat units derived from the at least one crosslinking comonomer, where the sum total of the proportions by weight of the repeat units derived from the at least one first monomer and from the at least one comonomer and from the at least one further free-radically polymerizable, ethylenically unsaturated monomer and from the at least one crosslinking comonomer is 100% by weight.

In one embodiment of said use, the at least one first monomer is N-vinylpyrrolidone, and the at least one comonomer is selected from the group consisting of vinylphosphonic acid, 2-acrylamido-2-methylpropanesulfonic acid and combinations of these monomers, and the copolymer comprises, based on the total mass of the repeat units in the copolymer, 70%-99.5% by weight, preferably 80%-99% by weight, preferably 85%-98% by weight, of repeat units derived from N-vinylpyrrolidone, and 0.5%-30% by weight, preferably 1%-20% by weight, preferably 2%-15% by weight, of repeat units derived from the at least one comonomer, where the sum total of the proportions by weight of the repeat units derived from the at least one first monomer and from the at least one comonomer is 100% by weight.

In one embodiment of said use, the at least one first monomer is N-vinyl-2-caprolactam, and the at least one comonomer is selected from the group consisting of vinylphosphonic acid, 2-acrylamido-2-methylpropanesulfonic acid and combinations of these monomers, and the copolymer comprises, based on the total mass of the repeat units in the copolymer, 70%-99.5% by weight, preferably 80%-99% by weight, preferably 85%-98% by weight, of repeat units derived from N-vinylpyrrolidone, and 0.5%-30% by weight, preferably 1%-20% by weight, preferably 2%-15% by weight, of repeat units derived from the at least one comonomer, where the sum total of the proportions by weight of the repeat units derived from the at least one first monomer and from the at least one comonomer is 100% by weight.

The present invention further provides for the use of a composition comprising a peroxidic compound, where this peroxidic compound is selected from the group consisting of an organic peroxide compound and hydrogen peroxide, especially selected from the group consisting of an organic hydroperoxide and hydrogen peroxide, especially selected from the group consisting of tert-butyl hydroperoxide, cumene hydroperoxide and hydrogen peroxide, and is especially hydrogen peroxide, and a copolymer as defined in any of the above paragraphs that describe the subject matter of the present invention and particular embodiments, for bleaching of teeth, where this composition is preferably obtainable by spray-drying, and where this composition, per 100 g of copolymer, comprises preferably 1-32 g, especially 3-30 g, especially 8-28 g, of peroxidic compound.

In one embodiment of said use, the composition is present in a formulation selected from the group consisting of a toothpaste, a mouthwash, a gel for tooth bleaching and an oral spray, wherein the composition is preferably present in the formulation in such an amount that the formulation comprises 0.01% to 5% by weight, especially 0.1% to 4% by weight, especially 0.3% to 3% by weight, of peroxidic compound.

In one embodiment of said use, the formulation comprises further known auxiliaries and ingredients for these formulations. If the formulation is a toothpaste, this is preferably essentially anhydrous. "Essentially anhydrous" means less than 8% by weight, especially less than 5% by weight, especially less than 3% by weight, of water. The toothpaste may especially comprise, as carrier material, polyethylene oxide or polyethylene oxide-polypropylene oxide copolymers.

The formulation may comprise those auxiliaries and ingredients as disclosed in US 2012/0058059.

The present invention further provides a copolymer comprising repeat units derived from a first monomer which is N-vinylpyrrolidone, at least one comonomer which is selected from the group consisting of vinylphosphonic acid, 2-acrylamido-2-methylpropanesulfonic acid and combinations of these monomers, optionally at least one further free-radically polymerizable, ethylenically unsaturated monomer, and optionally at least one crosslinking comonomer having at least two free-radically polymerizable, ethylenically unsaturated groups in the molecule.

In one embodiment of the copolymer, the at least one crosslinking comonomer is selected from the group consisting of N,N'-divinylethyleneurea, N,N'-divinylpropyleneurea, N,N'-divinylimidazolid-2-one, N-vinyl-2-ethylidenepyrrolidone, N-vinyl-3-ethylidenepyrrolidone, methylenebisacrylamide, an allyl ether, a vinyl ether, a (meth)acrylic ester, a (meth)acrylamide of an alcohol or of an amine having more than two functional groups, and combinations of these monomers.

In one embodiment of the copolymer, the copolymer comprises, based on the total mass of the repeat units of the copolymer,
- 70%-99.5% by weight of repeat units derived from the at least one first monomer,
- 0.5%-30% by weight of repeat units derived from the at least one comonomer,
- 0% to 20% by weight of repeat units derived from the at least one further free-radically polymerizable, ethylenically unsaturated monomer,
- 0%-10% by weight of repeat units derived from the at least one crosslinking comonomer,
- where the sum total of the proportions by weight of the repeat units derived from the at least one first monomer and from the at least one comonomer and from the at least one further free-radically polymerizable, ethylenically unsaturated monomer and from the at least one crosslinking comonomer is 100% by weight.

In one embodiment of the copolymer, the copolymer comprises, based on the total mass of the repeat units in the copolymer,
- 70%-99.5% by weight of repeat units derived from N-vinylpyrrolidone, and
- 0.5%-30% by weight of repeat units derived from the at least one comonomer,
- where the sum total of the proportions by weight of the repeat units derived from the at least one first monomer and from the at least one comonomer is 100% by weight.

The present invention further provides a composition comprising a peroxidic compound, where this peroxidic compound is selected from the group consisting of an organic peroxide compound and hydrogen peroxide, especially selected from the group consisting of an organic hydroperoxide and hydrogen peroxide, especially selected from the group consisting of tert-butyl hydroperoxide, cumene hydroperoxide and hydrogen peroxide, and is especially hydrogen peroxide, and a copolymer as defined in the preceding paragraphs, where this composition is preferably obtainable by spray-drying, and where this composition, per 100 g of copolymer, comprises preferably 1-32 g, especially 3-30 g, especially 8-28 g, of peroxidic compound.

The present invention further provides a formulation selected from the group consisting of a toothpaste, a mouthwash, a gel for tooth bleaching and an oral spray, comprising this composition.

The present invention further provides a method of bleaching teeth, comprising the contacting of the teeth with a composition—which may be present in the formulation of the invention as disclosed in the present document—comprising a peroxidic compound and a copolymer, where the peroxidic compound and the copolymer are both those as disclosed in accordance with the invention in the present document.

The copolymer according to the invention and the copolymer for use in accordance with the invention dissolve to a certain degree in water (saliva). It has a good affinity for teeth (see QCM measurements in the examples section of the present document). This means that the peroxidic compounds, especially H2O2, are released to an enhanced degree at the tooth, which leads to enhanced whitening of the teeth.

Examples of monomers comprising at least one phosphonic acid group are alkanol phosphates of the formula RO—P($=$O)(OH)$_2$ where R is an alkyl group, preferably having 1 to 30 carbon atoms.

Examples of monomers comprising at least one phosphonic acid group are vinylphosphonic acid, monovinyl phosphate, allylphosphonic acid, monoallyl phosphate, 3-butenylphosphonic acid, mono-3-butenyl phosphate, mono(4-vinyloxybutyl) phosphate, phosphonoxyethyl acrylate, phosphonoxyethyl methacrylate, mono(2-hydroxy-3-vinyloxypropyl) phosphate, mono(1-phosphonoxymethyl-2-vinyloxyethyl) phosphate, mono(3-allyloxy-2-hydroxypropyl) phosphate, mono-2-(allyloxy-1-phosphonoxymethylethyl) phosphate, 2-hydroxy-4-vinyloxymethyl-1,3,2-dioxaphosphole, 2-hydroxy-4-allyloxymethyl-1,3,2-dioxaphosphole and esters of hydroxyethyl or hydroxypropyl (meth)acrylate with (poly)phosphoric acid.

Examples of monomers comprising at least one sulfonic acid group are allylsulfonic acid, methallylsulfonic acid, styrenesulfonic acid, toluenesulfonic acid, vinylsulfonic acid, allyloxybenzenesulfonic acid or 2-acrylamido-2-methylpropanesulfonic acid, 2-((meth)-acryloyl)ethylsulfonic acid, 2-acrylamidomethyldodecylsulfonic acid and 3-(meth)-acryloyloxypropanesulfonic acid.

Examples of ethylenically unsaturated dicarboxylic acids are itaconic acid, maleic acid, mesaconic acid, citraconic acid, fumaric acid and methylenemalonic acid.

Examples of ethylenically unsaturated dicarboxylic anhydrides are itaconic acid, maleic acid, mesaconic acid, citraconic acid, fumaric acid and methylenemalonic acid.

The repeat units of the comonomer, when they comprise acid groups, may take the form of free acid groups in the copolymer of the invention, or they may be in deprotonated form together with one or more different cations. Cations may, for example, be alkali metal cations or ammonium ions. Further suitable cations are formed by protonation of bases, for example of ammonia, organic amines such as aminomethylpropanol, triethanolamine, ethanolamine, hydrophobically modified amines such as N—(N,N-bis(hydroxyethyl)aminopropyl)-N-hydroxyethyloctadecylamine or 9-octadecenylamine, or naturally occurring amines such as lysine, histidine or cadaverine.

The copolymer of the invention is preferably water-soluble. "Water-soluble" means that the solubility of the copolymer of the invention in water at 20° C. is at least 45% by weight.

The copolymer of the invention typically has a K value within a range from 10 to 120, preferably from 16 to 60, more preferably from 20 to 45. The K values are measured in accordance with H. Fikentscher, Cellulose-Chemie 13, pages 48-64 and pages 71-94 (1932) (1% in 5% by weight aqueous saline solution at 22° C. and pH 7). The K value is a measure of the mean molar mass of a polymer. The higher the K value, the higher the mean molar mass.

In the case that the K values are too small, there are many oxidizable end groups in the copolymer of the invention, which is disadvantageous. In the case that the K values are too high, difficulties can arise in the spray-drying of the copolymers of the invention.

Preparation of the Copolymers of the Invention

The copolymers of the invention can be obtained by free-radical copolymerization. Free-radical initiators used may be standard azo, peroxy and redox initiators. Preference is given to using $H_2O_2$/copper initiators or 2,2'-azobis(2-amidinopropane) dihydrochloride. The reaction temperature in the copolymerization is typically between 30 and 100° C.

The preparation of the copolymers can be conducted by the method of solution polymerization in water, in alcohols, for example ethanol or isopropanol, or in water/alcohol mixtures. Preference is given to conducting the copolymerization in water. The solids content is typically between 5% and 75% by weight, preferably between 25%-45% by weight.

The optionally crosslinked copolymer of the invention can be prepared by various methods, for example by the method of gel polymerization—preferably in an aqueous medium—or by the method of inverse emulsion or suspension polymerization, or by the method of water-in-water polymerization in an aqueous biphasic mixture. A further method of preparing the copolymer of the invention is a popcorn polymerization of the monomers in water as solvent. Popcorn polymers are crosslinked and water-insoluble. They can be formulated as ground particles.

Production of the Composition Comprising a Peroxidic Compound, Especially H2O2, and a Copolymer (Also Called "Copolymer-Peroxide Complexes") According to the Present Invention Peroxides (also called "peroxidic compounds") used may be organic peroxides or $H_2O_2$. Preference is given to using hydroperoxides such as tert-butyl hydroperoxide or cumene hydroperoxide, or else $H_2O_2$. Very particular preference is given to using $H_2O_2$. The peroxide is preferably used as an aqueous solution in a concentration of 10%-70% by weight, preferably 30%-50% by weight.

The peroxide is preferably used in amounts of 1%-40% by weight, more preferably 2%-30% by weight, most preferably 5%-25% by weight, based on the copolymer-$H_2O_2$ complex.

Preference is given to mixing an aqueous solution of a copolymer of the invention with the peroxide and subjecting the resultant solution to a suitable drying method, for example roll drying, fluidized bed drying, freeze-drying or spray-drying. The solutions can be mixed before or during the drying method.

Preference is given to producing the complexes by spray-drying of a copolymer-$H_2O_2$ solution by the method as described in the claims of EP 0 714 919 A2.

Water-insoluble polymer-peroxide complexes, according to the method of DE 19455380 A1, can be admixed with H2O2 in aqueous suspension, filtered off and then dried by various methods, for example in a paddle dryer.

$H_2O_2$ complexes of the popcorn polymers are preferably prepared by the fluidized bed method. This involves spraying the polymer with an $H_2O_2$ solution and drying it in the defined air stream. The temperature of the feed air is typically between 25 and 80° C., and that of the output air 25 to 70° C. More detailed descriptions can be found especially on page 3 starting from line 47 in DE 4344131 A1. With the aid of this method, it is possible to obtain free-flowing powder having a water content of less than 5% by weight.

Use

The copolymer-peroxide complexes of the invention are preferably used in dental treatment products, especially in toothpastes. The copolymer-peroxide complexes of the invention are also used in dental treatment compositions selected from the group consisting of a mouthwash, a gel for tooth bleaching and an oral spray. Most preferably, these dental treatment products are essentially anhydrous. "Essentially anhydrous" means less than 8% by weight, especially less than 5% by weight, especially less than 3% by weight, of water. High amounts of water reduce the stability of the copolymer-peroxide complex.

EXAMPLES

The following abbreviations and designations are used hereinafter:

VP: N-vinylpyrrolidone
VCap: N-vinyl-2-caprolactam
AMPS: 2-acrylamido-2-methylpropanesulfonic acid
VPA: vinylphosphonic acid
Wako V 50: 2,2'-azobis(2-methylpropionamidine) dihydrochloride (a polymerization initiator)
K value: K value according to Fikentscher
% means % by weight unless stated otherwise.

Example 1a: VP-AMPS Copolymer (in a Mass Ratio of 90 to 10), Semibatchwise Mode

A flask of capacity 2.5 liters was equipped with a stirrer, a cooling unit, an internal thermometer and a metering apparatus. The latter was charged with 920 g of demineralized water (DM water), 0.55 g of ammonia solution (25%) and 256 g of N-vinylpyrrolidone (VP), and heated up to internal temperature 75° C. under a nitrogen atmosphere. The initiator system (27 g of $H_2O_2$ (30% strength) in 138 g of DM water and 0.12 g of 0.09% copper(II) chloride solution (CuCl$_2$ soln.)) was metered into the reaction mixture via separate reservoir vessels over the course of 8 h. Commencing with the addition of initiator, over a period of 4 h, a mixture of 464 g of VP, 80 g of 2-acrylamido-2-methylpropanesulfonic acid (AMPS), 30.85 g of sodium hydroxide (NaOH) and 56 g of DM water was metered in continuously. After all the coreactants had been added, the reaction mixture was kept at internal temperature 75° C. for a further 2 h and then cooled down to room temperature.

The solids content of the reaction product was 43%. The analysis of the 0.01 g/cm$^3$ polymer solution (this polymer solution resulted from dilution of the reaction mixture obtained) in a 5% by weight aqueous saline solution gave a K value of 33.

Example 1b: VP-AMPS Copolymer (in a Mass Ratio of 90 to 10), K Value 66

A flask of capacity 2.5 liters was equipped with a stirrer, a cooling unit, an internal thermometer and a metering apparatus. The latter was charged with 920 g of DM water, 0.55 g of ammonia solution (25%) and 256 g of VP, and heated up to internal temperature 85° C. under a nitrogen atmosphere. 9 g of the Wako V 50 initiator were blended with 157 g and added to the reaction mixture within 5.5 h. At the same time, over a period of 4 h, a mixture of 464 g of VP, 80 g of AMPS, 30.85 g of NaOH and 56 g of DM water was metered in continuously. Commencing at the same juncture, via a further feed vessel, a further 72 g of 25% ammonia solution were added to the reaction mixture within 6.5 h. On completion of addition, the internal temperature was kept at 85° C. for a further 2 h.

The product thus produced is viscous, has a solids content of 44% and a K value of 66 (according to analysis of a 0.01 g/cm$^3$ polymer solution (this polymer solution resulted from dilution of the reaction mixture obtained) in a 5% by weight aqueous saline solution).

Example 1c: VP-AMPS Copolymer (in a Mass Ratio of 90 to 10), Batchwise Mode

A flask of capacity 2.5 liters was equipped with a stirrer, a cooling unit, an internal thermometer and a metering apparatus. The latter was charged with 808 g of DM water, 1.18 g of ammonia solution (25%), and also 379.27 g of VP and 84.2 g of AMPS, and heated up to internal temperature 85° C. under a nitrogen atmosphere. Prior to attainment of the target temperature, from three different flasks, 8.77 g of $H_2O_2$ (30%), a mixture of 1.05 g of DM water and 0.08 g of $CuCl_2$, and 1.71 g of ammonia solution (25%) were added to the reaction mixture over a period of 2 h. Subsequently, the internal temperature was kept constant at 85° C. for a further 2 h.

The product thus produced has a solids content of 33% and a K value of 31 (according to analysis of a 0.01 g/cm$^3$ polymer solution (this polymer solution resulted from dilution of the reaction mixture obtained) in a 5% by weight aqueous saline solution).

Example 2: VP-AMPS Copolymer (in a Mass Ratio of 95 to 5)

Analogously to example 1a, 276 g of N-vinylpyrrolidone were used in the initial charge and 484 g of VP in the monomer mixture, and also 40 g of AMPS. The monomer mixture was metered into the reaction mixture over a period of 4 h. A copolymer with 95% by weight of VP and 5% by weight of AMPS was obtained. The product obtained has a solids content of 42% and the analysis of the polymer solution diluted to 0.01 g/cm$^3$ in a 5% by weight aqueous saline solution gave a K value of 38.

Example 3: VP-VPA Copolymer (in a Mass Ratio of 90 to 10)

A flask of capacity 2.5 liters was equipped with a stirrer, a cooling unit, an internal thermometer and a metering apparatus. The latter was charged with 950 g of DM water, 74 g of NaOH and 50 g of vinylphosphonic acid (VPA). Under a nitrogen atmosphere, the reaction mixture was heated to 85° C. 450 g of VP and a mixture of 25 g of Wako V 50 and 237.5 g of DM water were metered into the reaction mixture within 8 h. Subsequently, the internal temperature was kept constant at 85° C. for a further 2 h.

In this way, a viscous yellowish solution having a solids content of 28% and a K value of 36 (0.01 g/cm$^3$ polymer solution in a 5% by weight aqueous saline solution) was obtained.

Example 4: VP-VPA Copolymer (in a Mass Ratio of 95 to 5)

The reaction was conducted analogously to example 3, except that the VPA content in the initial charge was reduced to 25 g and the NaOH content to 25 g. The amount of VP to be metered in was increased to 430 g; the internal temperature was kept constant at 85° C. Finally, the product was cooled to room temperature.

The product obtained has a solids content of 31% and the analysis of the 0.01 g/cm$^3$ polymer solution in a 5% by weight aqueous saline solution gave a K value of 50.

Example 5: Spray-Drying of the Polymer from Example 1a 1641 g of a 40% by weight aqueous solution of a copolymer that comprised 90% by weight of VP and 10% by weight of AMPS (according to example 1a) were mixed with 412 g of a 50% by weight $H_2O_2$ solution and 300 g of water. The mixture obtained was spray-dried. The feed temperature of the nitrogen during the spray-drying was 162-164° C., and the outlet temperature was kept between 75° C. and 78° C. The throughput was 746 g/h. In this way, a free-flowing polymer was obtained.

Example 6: Spray-Drying of the Polymer from Example 3

1001 g of a 30% by weight aqueous solution of a copolymer that comprised 90% by weight of VP and 10% by weight of VPA (according to example 3) were mixed with 174 g of a 50% by weight $H_2O_2$ solution and 202 g of water. The mixture obtained was spray-dried. The feed temperature of the nitrogen during the spray-drying was 155-160° C., and the outlet temperature was kept between 68° C. and 70° C. The throughput was 910 g/h. In this way, a free-flowing polymer was obtained.

Study of Tooth Affinity

The tooth affinity of the spray-dried polymers was characterized with the aid of a quartz crystal microbalance (QCM). The sensor used was a quartz crystal coated with nanocrystalline hydroxyapatite (QSX 327 HA, manufacturer: BioLin Scientific AB, Stockholm). Before each experiment, water was first passed over the crystal at 36° C. at a rate of 50 mL/minute, and the resonance frequency thereof was measured. Subsequently, the solution of the polymer to be tested in water (concentration: 50 ppm)—adjusted to a pH of 7.0—was passed over the sensor under the same conditions. Adsorption of the polymer is manifested in a decrease in the resonance frequency over time. The Sauerbrey equation can be used to convert the change in frequency measured to masses or layer thicknesses actually adsorbed.

| Polymer | Example | Decrease in frequency |
|---|---|---|
| "K-30 polyvinylpyrrolidone" | non-inventive | 0 Hz |
| VP/AMPS copolymer Molar ratio 90 to 10 | 1 | 3 Hz |
| VP/VPA copolymer Molar ratio 90 to 10 | 3 | 3 Hz |

"K-30 polyvinylpyrrolidone" is Luviskol ® K30 PDR, available from BASF SE.

The examples show the affinity of the polymers according to the invention for tooth surfaces.

FURTHER EXAMPLES

Example 7: VCap-AMPS Copolymer (in a Mass Ratio of 90/10)

A flask of capacity 2.5 liters was equipped with a stirrer, a cooling unit, an internal thermometer and a metering apparatus. The latter was charged with 729 g of DM water, 0.32 g of ammonia solution (25%), and also 360 g of VCap and 80 g of AMPS, and heated up to internal temperature 85° C. under a nitrogen atmosphere. Prior to attainment of the target temperature, from three different flasks, 27.72 g of H2O2 (15%), a mixture of 12.4 g of DM water and 0.08 g of CuCl$_2$ solution, and 14.4 g of ammonia solution (2.5%) were added to the reaction mixture over a period of 2 h. Subsequently, the internal temperature was kept constant at 85° C. for a further 2 h.

The product thus produced had a solids content of 29% and a K value of 16 (according to analysis of a 0.01 g/cm$^3$ polymer solution (this polymer solution resulted from dilution of the reaction mixture obtained) in a 5% by weight aqueous saline solution).

The VCap-AMPS copolymer solution was subsequently admixed 1:1 with a 50% by weight H2O2 solution and introduced into a petri dish. This solution was dried at 45° C. in a vacuum cabinet for 12 h. In this way, it was possible to obtain a transparent VCap-AMPS copolymer-H2O2 complex film.

Example 8: Prevention of Discoloration and Whitening of an Already Stained Apatite Powder In order to show the whitening properties and discoloration-preventative capacities of the copolymer-H2O2 complex, the following experiments were conducted:
1. Control experiment: staining of apatite with coffee
2. Preventative properties against discoloration
3. Whitening properties on the discolored apatite
Chemicals Used
  spray-dried PVP-AMPS copolymer-H2O2 complex according to example 5
  Coffee: Contal Gold Instant Kaffee 100% Arabica from Penny Markt GmbH
  Apatite: hydroxyapatite from Sigma Aldrich CAS: 1306-06-5
Procedure for the Discoloration Experiments:
  For 1:10 g of apatite were stirred with 30 mL of coffee (2% by weight) at 37° C. for 15 min and then centrifuged.
  The solids were then washed with 30 mL of DM water and centrifuged.
  Then the following wash step was conducted twice: The solids were stirred with 30 mL of DM water at 37° C. for 15 min and then centrifuged off.
  Finally, the solids were dried in a vacuum cabinet at 45° C. for 12 h and then crushed with a mortar and pestle.
  For 2: 10 g of PVP-AMPS copolymer-H2O2 complex were dissolved in 30 g of water and blended with 10 g of apatite. This mixture was stirred for 15 min and then centrifuged. Subsequently, the solids were stirred with 30 mL of coffee (2% by weight) at 37° C. for 15 min and centrifuged.
  Workup was analogous to 1:
  The solids were washed with 30 mL of DM water and centrifuged.
  Then the following wash step was conducted twice: The solids were stirred with 30 mL of DM water at 37° C. for 15 min and then centrifuged off.
  Finally, the solids were dried in a vacuum cabinet at 45° C. for 12 h and then crushed with a mortar and pestle.
  For 3: Discoloration of the Apatite Analogously to 1:
  10 g of apatite were stirred with 30 mL of coffee (2% by weight) at 37° C. for 15 min and then centrifuged.
  The solids were then washed with 30 mL of DM water and centrifuged.
  Then the following wash step was conducted twice: The solids were stirred with 30 mL of DM water at 37° C. for 15 min and then centrifuged off.
  The stained apatite was stirred with 10 g of polymer (PVP-AMPS copolymer-H2O2 complex) in 30 g of DM water at 37° C. for 15 min and then centrifuged.
  Finally, the solids were dried in a vacuum cabinet at 45° C. for 12 h and then crushed with a mortar and pestle.
Observations for 1, 2 and 3:
  All three samples are brownish in color. Sample 1 (control experiment, stained with coffee) is darker than sample 2 (preventively treated with copolymer-H2O2 complex, prior to staining with coffee). Sample 2 in turn is darker than sample 3 (treated with copolymer-H2O2 complex after staining with coffee). These examples show the efficacy of the copolymer-H2O2 complex both for preventative measures against unwanted discoloration and for whitening in the case of existing discoloration. Apatite is very similar to enamel. So it can be assumed that corresponding whitening effects can also be achieved in teeth.

The invention claimed is:
1. A method of bleaching teeth comprising contacting the teeth with a composition comprising a peroxidic compound selected from the group consisting of an organic peroxide compound and hydrogen peroxide,
  and a copolymer comprising repeat units derived from
    at least one first monomer which is selected from the group consisting of N-vinylpyrrolidone (N-vinyl-2-pyrrolidone), N-vinyl-2-piperidone, N-vinyl-3-methylpyrrolidinone, N-vinyl-3-methylpiperidone, N-vinyl-3-methylcaprolactam, N-vinyl-4-methylpyrrolidinone, N-vinyl-4-methyl-2-pyrrolidone, N-vinyl-4-methylpiperidone, N-vinyl-4-methylcaprolactam, N-vinyl-5-methylpyrrolidinone, N-vinyl-5-ethyl-2-pyrrolidone, N-vinyl-4-methylpiperidone, N-vinyl-3-ethylpyrrolidinone, N-vinyl-4,5-dimethylpyrrolidinone, N-vinyl-5,5-dimethylpyrrolidinone, N-vinyl-3,3,5-trimethylpyrrolidinone, N-vinyl-5-methyl-5-ethylpyrrolidinone, N-vinyl-3,4,5-trimethyl-3-ethylpyrrolidinone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-2-caprolactam, N-vinyl-7-methylcaprolactam, N-vinyl-7-ethylcaprolactam, N-vinyl-3,5-dimethylcaprolactam, N-vinyl-4,6-dimethylcaprolactam, N-vinyl-3,5,7-trimethylcaprolactam, N-vinyl-2-valerolactam,

N-vinylhexahydro-2-azepinone, N-vinyloctahydro-2-azocinone, N-vinyloctahydro-2-azoninone, N-vinyldecahydro-2-azecinone, and combinations of these monomers, at least one comonomer which is selected from the group consisting of a monomer comprising at least one phosphoric ester group, a monomer comprising at least one phosphonic acid group, a monomer comprising at least one sulfonic acid group, an ethylenically unsaturated dicarboxylic acid, an ethylenically unsaturated dicarboxylic anhydride, and combinations of these monomers, optionally at least one further free-radically polymerizable, ethylenically unsaturated monomer, and optionally at least one crosslinking comonomer having at least two free-radically polymerizable, ethylenically unsaturated groups in the molecule.

2. The method according to claim 1, wherein the at least one first monomer is N-vinylpyrrolidone.

3. The method according to claim 1, wherein the at least one first monomer is N-vinyl-2-caprolactam.

4. The method according to claim 1, wherein the at least one comonomer is selected from the group consisting of maleic acid, maleic anhydride, fumaric acid, vinylphosphonic acid, 2-acrylamido-2-methylpropanesulfonic acid, acrylamidopropanesulfonic acid, and combinations of these monomers.

5. The method according to claim 1, wherein the at least one comonomer is selected from the group consisting of vinylphosphonic acid, 2-acrylamido-2-methylpropanesulfonic acid, and combinations of these monomers.

6. The method according to claim 1, wherein the at least one crosslinking comonomer is selected from the group consisting of N,N'-divinylethyleneurea, N,N'-divinylpropyleneurea, N,N'-divinylimidazolid-2-one, N-vinyl-2-ethylidenepyrrolidone, N-vinyl-3-ethylidenepyrrolidone, methylenebisacrylamide, an allyl ether, a vinyl ether, a (meth)acrylic ester, a (meth)acrylamide of an alcohol or of an amine having more than two functional groups, and combinations of these monomers.

7. The method according to claim 1, wherein the copolymer comprises, based on the total mass of the repeat units in the copolymer, 70%-99.5% by weight of repeat units derived from the at least one first monomer, 0.5%-30% by weight of repeat units derived from the at least one comonomer, 0% to 20% by weight of repeat units derived from the at least one further free-radically polymerizable, ethylenically unsaturated monomer, 0%-10% by weight of repeat units derived from the at least one crosslinking comonomer, where the sum total of the proportions by weight of the repeat units derived from the at least one first monomer and from the at least one comonomer and from the at least one further free-radically polymerizable, ethylenically unsaturated monomer and from the at least one crosslinking comonomer is 100% by weight.

8. The method according to claim 1,
wherein the at least one first monomer is N-vinylpyrrolidone,
and wherein the at least one comonomer is selected from the group consisting of vinylphosphonic acid, 2-acrylamido-2-methylpropanesulfonic acid, and combinations of these monomers,
and wherein the copolymer comprises, based on the total mass of the repeat units in the copolymer,
70%-99.5% by weight of repeat units derived from N-vinylpyrrolidone, and
0.5%-30% by weight of repeat units derived from the at least one comonomer,
where the sum total of the proportions by weight of the repeat units derived from the at least one first monomer and from the at least one comonomer is 100% by weight.

9. The method according to claim 1,
wherein the at least one first monomer is N-vinyl-2-caprolactam,
and wherein the at least one comonomer is selected from the group consisting of vinylphosphonic acid, 2-acrylamido-2-methylpropanesulfonic acid, and combinations of these monomers,
and wherein the copolymer comprises, based on the total mass of the repeat units in the copolymer,
70%-99.5% by weight of repeat units derived from N-vinylpyrrolidone, and
0.5%-30% by weight of repeat units derived from the at least one comonomer,
where the sum total of the proportions by weight of the repeat units derived from the at least one first monomer and from the at least one comonomer is 100% by weight.

10. The method according to claim 1, wherein the peroxidic compound is selected from the group consisting of an organic hydroperoxide and hydrogen peroxide.

11. The method according to claim 1, wherein the composition is present in a formulation selected from the group consisting of a toothpaste, a mouthwash, a gel for tooth bleaching, and an oral spray.

12. The method according to claim 11, wherein the formulation comprises further known auxiliaries and ingredients for these formulations.

13. The method according to claim 10, wherein the peroxidic compound is selected from the group consisting of tert-butyl hydroperoxide, cumene hydroperoxide, and hydrogen peroxide.

14. The method of claim 1 wherein the peroxide compound is hydrogen peroxide.

* * * * *